(12) United States Patent
Cuscuna

(10) Patent No.: US 11,484,291 B2
(45) Date of Patent: Nov. 1, 2022

(54) INTERPOSER ELECTRICAL INTERCONNECT COUPLING METHODS, APPARATUSES, AND SYSTEMS

(71) Applicant: KONINKLIJKE PHILIPS N.V., Eindhoven (NL)

(72) Inventor: Dino Francesco Cuscuna, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 682 days.

(21) Appl. No.: 15/541,732

(22) PCT Filed: Jan. 2, 2016

(86) PCT No.: PCT/IB2016/050004
§ 371 (c)(1),
(2) Date: Jul. 6, 2017

(87) PCT Pub. No.: WO2016/113638
PCT Pub. Date: Jul. 21, 2016

(65) Prior Publication Data
US 2018/0271494 A1  Sep. 27, 2018

Related U.S. Application Data

(60) Provisional application No. 62/102,656, filed on Jan. 13, 2015.

(51) Int. Cl.
*A61B 8/00* (2006.01)
*A61B 8/08* (2006.01)
*A61B 8/12* (2006.01)
*G10K 11/00* (2006.01)
*G01S 7/52* (2006.01)
*B06B 1/02* (2006.01)

(52) U.S. Cl.
CPC .......... *A61B 8/4494* (2013.01); *A61B 8/0883* (2013.01); *A61B 8/12* (2013.01); *A61B 8/445* (2013.01); *B06B 1/02* (2013.01); *G01S 7/52079* (2013.01); *G10K 11/004* (2013.01)

(58) Field of Classification Search
CPC ....... A61B 8/4494; A61B 8/0883; A61B 8/12; A61B 8/445; B06B 1/02; G10K 11/004; G01S 7/52079
See application file for complete search history.

(56) References Cited

U.S. PATENT DOCUMENTS 5,669,389 A   9/1997 Rottevelle et al.
5,882,310 A   3/1999 Marian
(Continued)

FOREIGN PATENT DOCUMENTS

| CN | 104011856 A | 8/2014 |
| JP | 2014057136 A | 3/2014 |
| WO | 2014051804 A1 | 6/2013 |

*Primary Examiner* — Bill Thomson
*Assistant Examiner* — Aminah Asghar

(57) ABSTRACT

Systems, methods, and apparatuses for coupling a flexible circuit to a printed circuit board (PCB) with an interposer in an ultrasound probe are disclosed. A bolster plate configured to compress the PCB, interposer, and flexible circuit against a transducer mount is disclosed. A method of coupling a bolster plate to a transducer mount with fasteners is disclosed. Fasteners that do not pass through the PCB, interposer, and flexible circuit are disclosed.

17 Claims, 10 Drawing Sheets

(56) References Cited

U.S. PATENT DOCUMENTS

| | | |
|---|---|---|
| 2004/0044285 A1 | 3/2004 | Flesch et al. |
| 2006/0116584 A1 | 6/2006 | Sudol et al. |
| 2007/0075717 A1* | 4/2007 | Kinghorn ............ G01R 1/07378 |
| | | 324/754.18 |
| 2010/0249598 A1 | 9/2010 | Smith et al. |
| 2011/0072970 A1* | 3/2011 | Slobodzian ............... A61N 7/00 |
| | | 95/249 |
| 2012/0143060 A1 | 6/2012 | Weekamp et al. |
| 2013/0002094 A1 | 1/2013 | Toda et al. |
| 2013/0188446 A1* | 7/2013 | Kubota ................. B06B 1/0622 |
| | | 367/7 |
| 2013/0261467 A1 | 10/2013 | Dausch et al. |
| 2013/0301395 A1* | 11/2013 | Hebrard .............. G01S 7/52079 |
| | | 367/189 |
| 2014/0058270 A1* | 2/2014 | Davidsen ............... A61B 8/546 |
| | | 600/472 |
| 2014/0269209 A1* | 9/2014 | Smith .................. A61B 8/4461 |
| | | 367/140 |
| 2015/0087988 A1* | 3/2015 | Lee ..................... A61B 8/4494 |
| | | 600/459 |
| 2015/0113904 A1* | 4/2015 | Sprague .................... E06B 3/70 |
| | | 52/656.9 |
| 2015/0150533 A1* | 6/2015 | Nakamura ........... A61B 8/5207 |
| | | 600/447 |
| 2015/0289851 A1 | 10/2015 | Kobayashi et al. |

\* cited by examiner

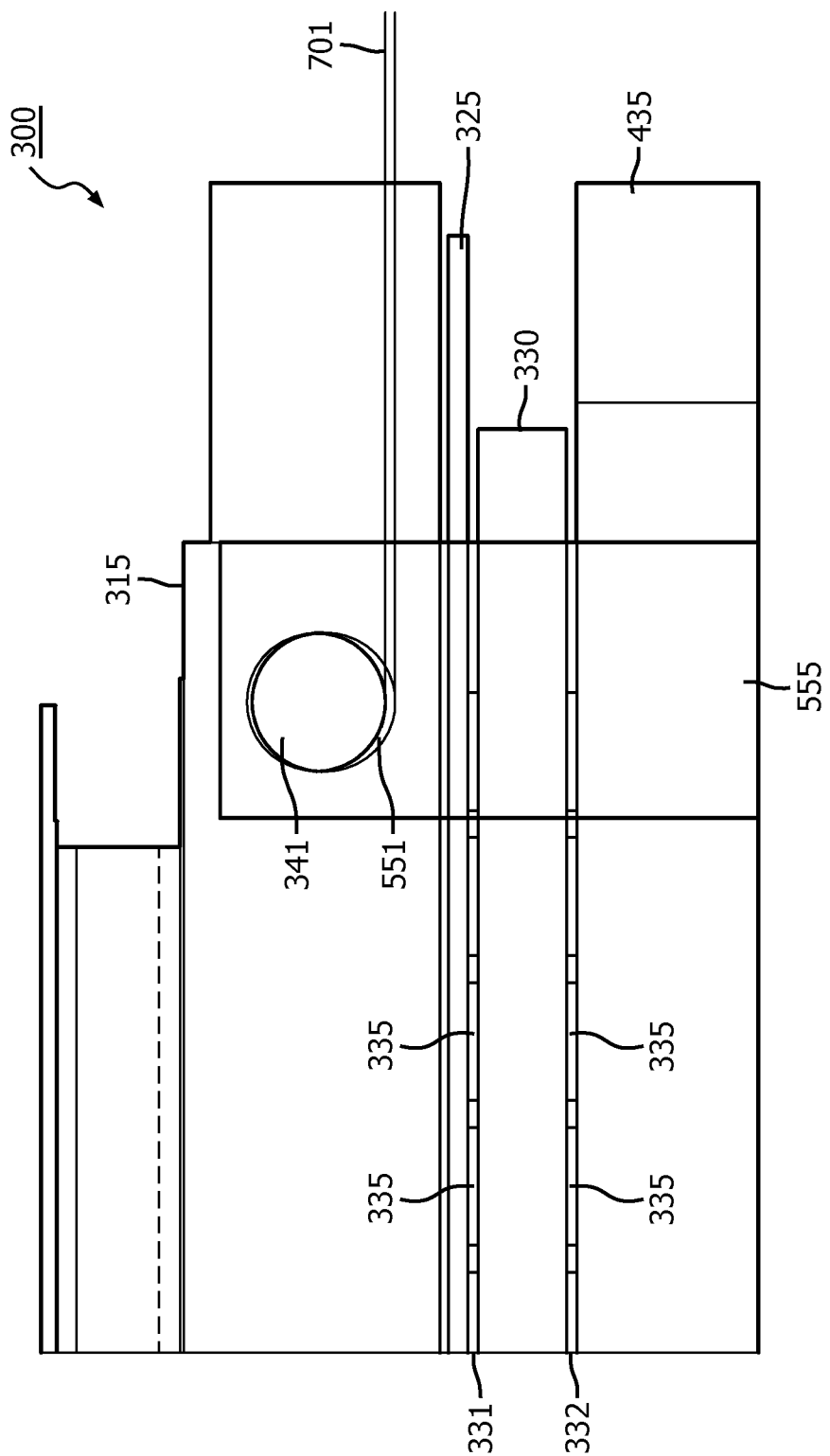

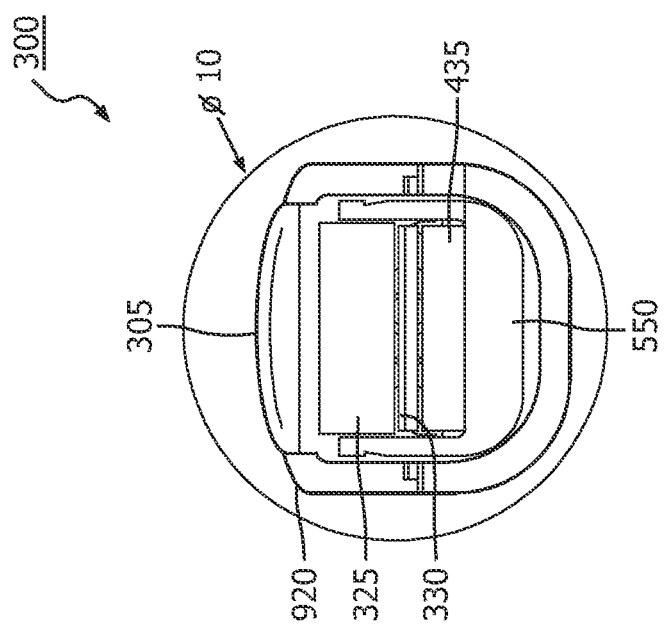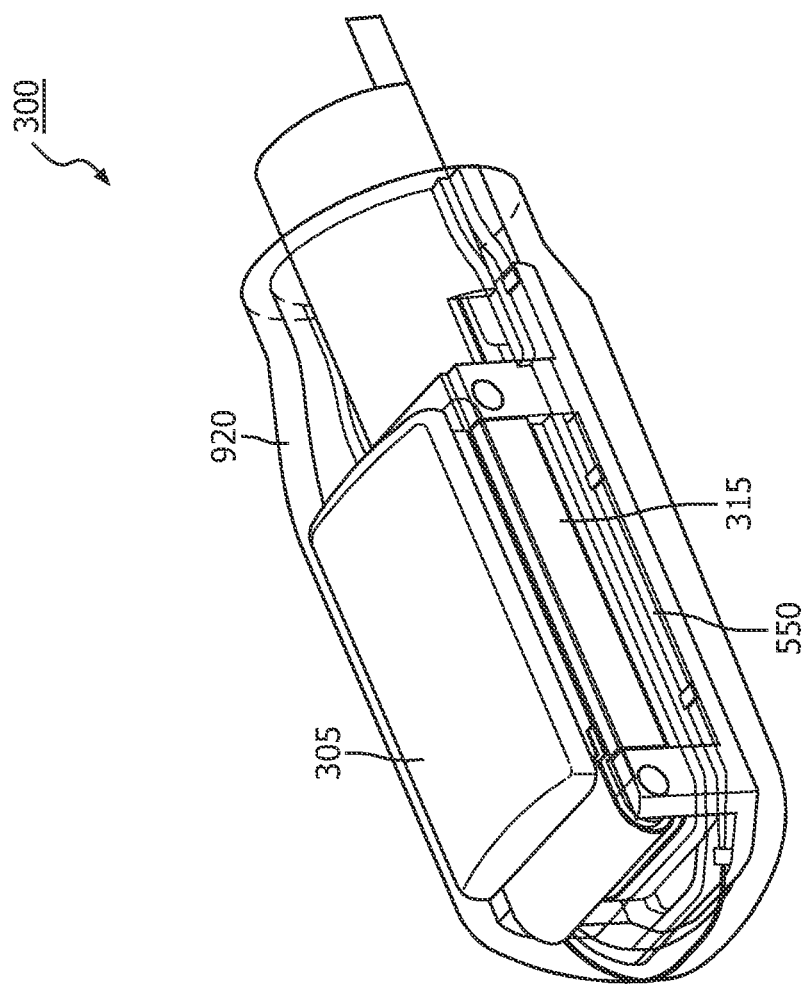
FIG. 7B
FIG. 7A

INTERPOSER ELECTRICAL INTERCONNECT COUPLING METHODS, APPARATUSES, AND SYSTEMS

This application is the U.S. National Phase application under 35 U.S.C. § 371 of International Application No. PCT/IB2016/050004, filed on Jan. 2, 2016, which claims the benefit of Provisional Application Ser. No. 62/102,656, filed Jan. 13, 2015. These applications are hereby incorporated by reference herein.

BACKGROUND

Transesophageal exam (TEE) and catheter ultrasound probes may be designed with limited external dimensions to access internal areas of the body that are inaccessible to traditional external ultrasound probes. For example, TEE probes may be positioned in the esophagus to perform echocardiography. To maintain limited external dimensions, a flexible circuit may be coupled to a transducer array and/or other hardware in the distal end of an endoscope-type device. The flexible circuit may then be coupled to a second flexible circuit that may provide power and communication with an ultrasound imaging system located at the proximal end of the device. The flexible circuits may provide a compact electrical assembly that fits within a probe designed to access internal areas of the body.

Coupling flexible circuits may be difficult and time consuming as surface soldering of individual connections may be required. The soldered connections between the flexible circuits may have poor reliability. The conductive traces within the flexible circuits may crack or break if the flexible circuit is deformed beyond a certain threshold and/or is deformed repeatedly. These deficiencies in coupling flexible circuits may lead to poor reliability of TEE and catheter ultrasound probes in a clinical setting. It may also increase the expense and difficulty of repairing malfunctioning probes. For example, it may not be feasible to de-solder the flexible circuits, so if one circuit is malfunctioning, both flexible circuits and associated components may need to be replaced.

SUMMARY

An example ultrasound probe according to an embodiment of the disclosure may include a transducer mount, a transducer stack coupled to an upper surface of the transducer mount, a flexible circuit coupled to the transducer stack and wrapped under the transducer mount, wherein the flexible circuit may cover a portion of a lower surface of the transducer mount, an interposer adjacent to the flexible circuit, opposite the lower surface of the transducer mount, a printed circuit board adjacent to the interposer opposite the flexible circuit, and a bolster plate adjacent to the printed circuit board wherein the bolster plate may be configured to be secured to the transducer mount and hold the printed circuit board in electrical contact with the flexible circuit through the interposer. The bolster plate may include a tab extending from a surface of the bolster plate to the transducer mount, wherein the tab may be configured to couple to the transducer mount and the tab may have a surface disposed against a side of the transducer mount. The tab may include a first opening and the transducer mount may include a second opening, and may further comprise a fastener which may be configured to fit within the first and second openings to couple the bolster plate to the transducer mount.

An example method according to an embodiment of the disclosure may include wrapping a flexible circuit coupled to a transducer stack under a transducer mount coupled to the transducer stack; positioning an interposer against the flexible circuit; positioning a printed circuit board against the interposer; compressing the printed circuit board, interposer, and flexible circuit against the transducer mount with a bolster plate; and coupling the bolster plate to the transducer mount. Coupling the bolster plate to the transducer mount may include passing a fastener through the bolster plate and transducer mount.

An example method according to an embodiment of the disclosure may include introducing a transesophageal ultrasound probe into a patient's mouth or nasal cavity, wherein the transesophageal ultrasound probe may include: a transducer mount, a transducer stack coupled to an upper surface of the transducer mount, a flexible circuit coupled to the transducer stack and wrapped under the transducer mount, wherein the flexible circuit may cover a portion of a lower surface of the transducer mount, an interposer adjacent to the flexible circuit, opposite the lower surface of the transducer mount, a printed circuit board adjacent to the interposer opposite the flexible circuit, and a bolster plate adjacent to the printed circuit board wherein the bolster plate may be configured to be secured to the transducer mount and hold the printed circuit board in electrical contact with the flexible circuit through the interposer; guiding the transesophageal ultrasound probe through the patient's laryngopharynx; guiding the transesophageal ultrasound probe into the patient's esophagus; positioning the transesophageal ultrasound probe in a desired location in the patient's gastrointestinal track; and acquiring an ultrasound image.

BRIEF DESCRIPTION OF THE DRAWINGS

FIG. 5 is a schematic illustration of the ultrasound probe illustrated in FIG. 4B according to an embodiment of the disclosure.

FIG. 7A is a schematic illustration of the ultrasound probe illustrated in FIG. 5 according to an embodiment of the disclosure.

FIG. 7B is a schematic illustration of an alternate view of the ultrasound probe illustrated in FIG. 7A according to an embodiment of the disclosure.

DETAILED DESCRIPTION

Figure 1A:
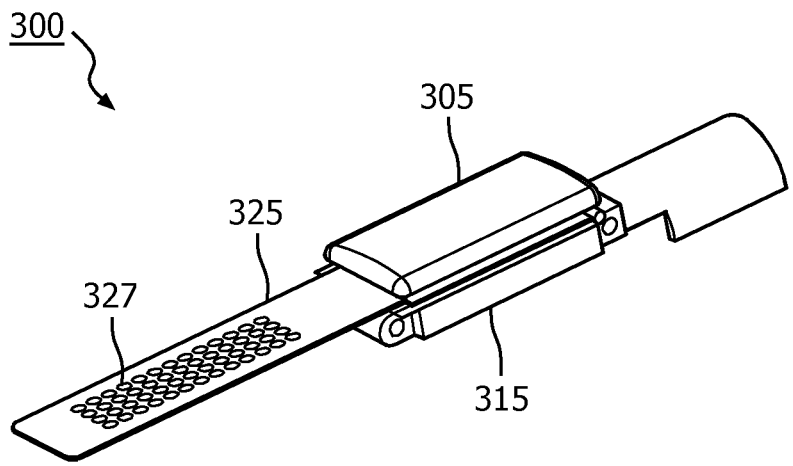
FIG. 1A is a schematic illustration of an ultrasound probe according to an embodiment of the disclosure.

The following description of certain exemplary embodiments is merely exemplary in nature and is in no way intended to limit the invention or its applications or uses. In the following detailed description of embodiments of the present systems and methods, reference is made to the accompanying drawings which form a part hereof, and in which are shown by way of illustration specific embodiments in which the described systems and methods may be practiced. These embodiments are described in sufficient detail to enable those skilled in the art to practice the presently disclosed systems and methods, and it is to be understood that other embodiments may be utilized and that structural and logical changes may be made without departing from the spirit and scope of the present system.

The following detailed description is therefore not to be taken in a limiting sense, and the scope of the present system is defined only by the appended claims. The leading digit(s) of the reference numbers in the figures herein typically correspond to the figure number, with the exception that identical components which appear in multiple figures are identified by the same reference numbers. Moreover, for the purpose of clarity, detailed descriptions of certain features will not be discussed when they would be apparent to those with skill in the art so as not to obscure the description of the present system.

In many traditional external probes, a flexible circuit is coupled to a transducer array. The flexible circuit may be able to bend, fold and/or twist. This may allow the flexible circuit to curve around another component and/or conform to a surface. The degree of flexibility of the flexible circuit may be determined, at least in part, by materials chosen for the flexible circuit (e.g. films, conductive elements, circuit components). The flexible circuit may include an insulating polymer film with conductive elements (e.g., wires) applied on one surface. A second insulating polymer film may be applied over the conductive elements and first polymer film. The conductive elements may be made of metals, conductive polymers, or other conductive materials. Some flexible circuits may include multiple alternating layers of elements and insulating film. The flexible circuit is then coupled to an interposer electrical interconnect, which electrically couples the flexible circuit to a printed circuit board. The printed circuit board (PCB) may provide power and control signals to the transducer array through the interposer and flexible circuit. The PCB may also receive signals from the transducer array through the interposer and flexible circuit. The interposer may eliminate the need to solder electrical connections directly between the flexible circuit and the PCB. The interposer may provide more reliable electrical coupling and easier disassembly. Individual components may be upgraded and/or replaced when faulty rather than replacing an entire flexible circuit/PCB assembly. The interposer may provide for ultrasound probes with greater reliability and easier repair of ultrasound probes that require maintenance.

An interposer may be secured to provide a uniform pressure distribution across all of the electrical interconnects included on the interposer to maintain electrical coupling between the flexible circuit and the PCB. Many traditional external ultrasound probes couple the interposer to the probe with two or more screws. However, the use of screws in some TEE and catheter probes may not be feasible due to the limited internal space. For example, the space requirements of the screws may prevent some desired electrical connections from being placed in a probe. The screws may also interrupt the heat flow path of the probe, reducing the thermal efficiency of the probe. In some probes, the dimensions of the probe may be small enough that the screws are within the acoustical path of a transducer stack in the probe and may introduce artifacts in the image acquired by the probe. The presence of artifacts may not be acceptable in some imaging applications.

For ultrasound probes with limited external dimensions (e.g. TEE and catheter), an alternative configuration for securing an interposer may be desirable to maintain adequate area on components for electrical connections and/or reduce image artifacts.

For TEE and catheter ultrasound probes, it may be desirable to secure the interposer without fasteners (e.g., screws) passing through the interposer and/or other components such as a PCB and flexible circuit. In some embodiments, a bolster plate may be placed under the PCB to hold the PCB, interposer, and flexible circuit together in a stack, and to maintain electrical connections between the components. In some embodiments, the bolster plate may compress the PCB, interposer, and flexible circuit against the transducer mount. The bolster plate may have tabs that extend from a surface of the bolster plate. The tabs may allow the bolster plate to be secured without the use of fasteners that pass through the PCB, interposer, and/or flexible circuit. This may allow a larger surface area of the components to be used for electrical connections. Potential damage to components during assembly and/or disassembly may be reduced when fasteners do not pass through the components. The fasteners may be offset such that they are not in the acoustical path of the ultrasound transducer array. The fasteners may be positioned such that the disruption of the thermal path is minimized.

Figure 1B:
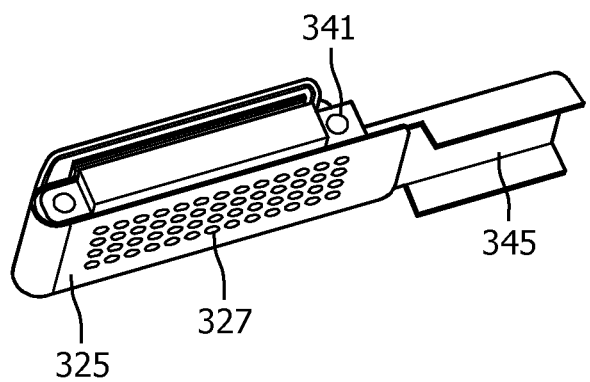
FIG. 1B is a schematic illustration of an additional view of the ultrasound probe illustrated in FIG. 1A according to an embodiment of the disclosure.

FIGS. 1A-C, 2A-B, 3A-B, and 4A-B are schematic illustrations of assembly of an ultrasound probe 300 according to an embodiment of the disclosure. Reference to the "top" and "bottom" orientation of the probe 300 in FIGS. 1A-3C, 2A-B, 3A-B, 4A-B is made to facilitate the description of the probe 300, and is not intended to limit embodiments of the disclosure to specific spatial orientations and/or configurations of the ultrasound probe 300. FIG. 1A is an isometric view of the top of the probe 300. A transducer stack 305 coupled to a transducer mount 315. The transducer mount 315 may include a backing layer below the transducer stack 305 and/or the transducer mount 315 may be implemented with a backing layer material. A flexible circuit 325 may be coupled to the transducer stack 305. The flexible circuit 325 includes conductors 327. FIG. 1B is an isometric view of the bottom of the probe 300. The flexible circuit 325 is wrapped under the transducer mount 315. The transducer mount 315 may include one or more openings 341 that run parallel to the plane of the transducer stack 305. The openings may extend from one side of the transducer mount 315 through to the other side of the transducer mount 315. The transducer mount 315 may further include notches 317 at ends 319 and 321. The notches 317 are disposed in the embodiment of FIG. 1 at opposite ends of the transducer mount, providing a step portion 323 between the notches 317. The one or more openings 341 may be positioned on either side of the transducer stack 305 such that they are outside the acoustical path of the transducer stack 305. The transducer mount 315 may include one or more flanges 345 in some embodiments. The flanges 345 may optionally be used for alignment of components within the probe 300, which may increase the speed and/or accuracy of assembly.

Figure 1C:
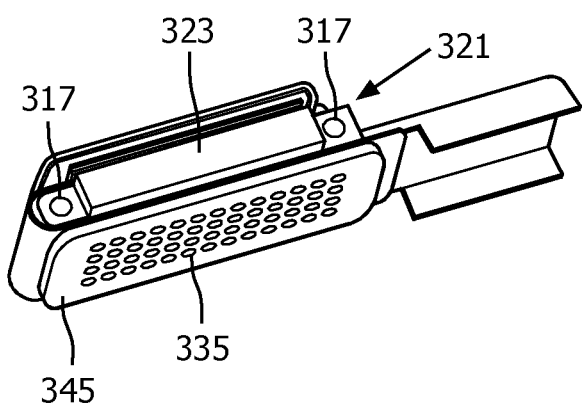
FIG. 1C is a schematic illustration of the ultrasound probe illustrated in FIG. 1A-B including an interposer according to an embodiment of the disclosure.

FIG. 1C is an isometric view of the bottom of the probe 300 with an interposer 330 positioned against the flexible circuit 325. The interposer 330 includes conductors 335 on both its sides. Some of the conductors 335 on one side of the interposer 330 may be electrically coupled to some of the conductors 335 on the opposite of the interposer 330. In some embodiments, the conductors 335 on one side may extend through the interposer 330 to the other side. One or more of the conductors 335 are electrically coupled to one or more of the conductors 327 of the flexible circuit 325 when positioned against the flexible circuit 325. Although not shown, the interposer 330 and/or transducer mount 315 may include flanges to aid in alignment during assembly in some embodiments.

Figure 2A:
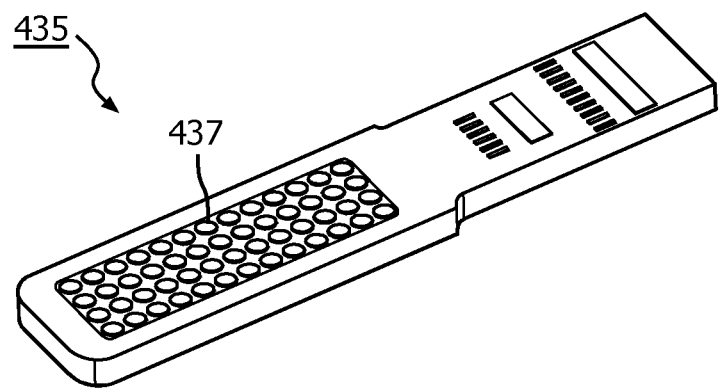
FIG. 2A is a schematic illustration of a printed circuit board according to an embodiment of the disclosure.
Figure 2B:
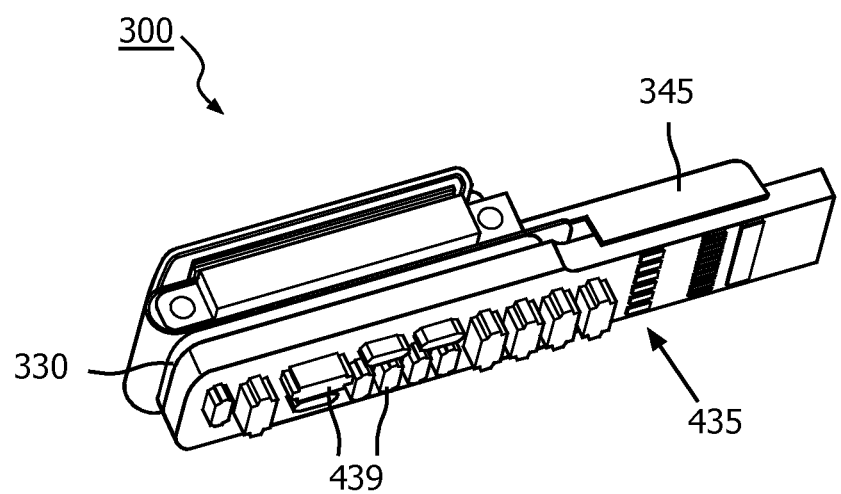
FIG. 2B is a schematic illustration of an ultrasound probe including the printed circuit board illustrated in FIG. 2A according to an embodiment of the disclosure.

FIG. 2A is an isometric view of the top of a printed circuit board (PCB) 435. The PCB 435 includes conductors 437. FIG. 2B is an isometric view of the bottom of the probe 300 with the PCB 435 positioned against the interposer 330. The PCB 435 may include circuits 439. The circuits 439 may be electrically coupled to the conductors 437. One or more of the conductors 437 may be electrically coupled to conductors 335 of the interposer 330 when the PCB 435 is positioned against the interposer 330. In the embodiment illustrated in FIG. 2B, the flanges 345 of the transducer mount 315 may be configured to position the PCB 435 against the interposer 330.

Figure 3A:
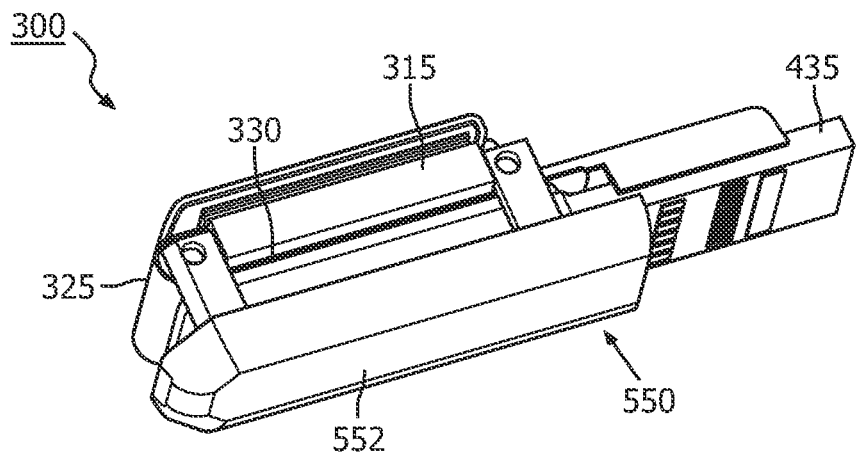
FIG. 3A is a schematic illustration of the ultrasound probe illustrated in FIG. 2B including a bolster plate according to an embodiment of the disclosure.
Figure 3B:
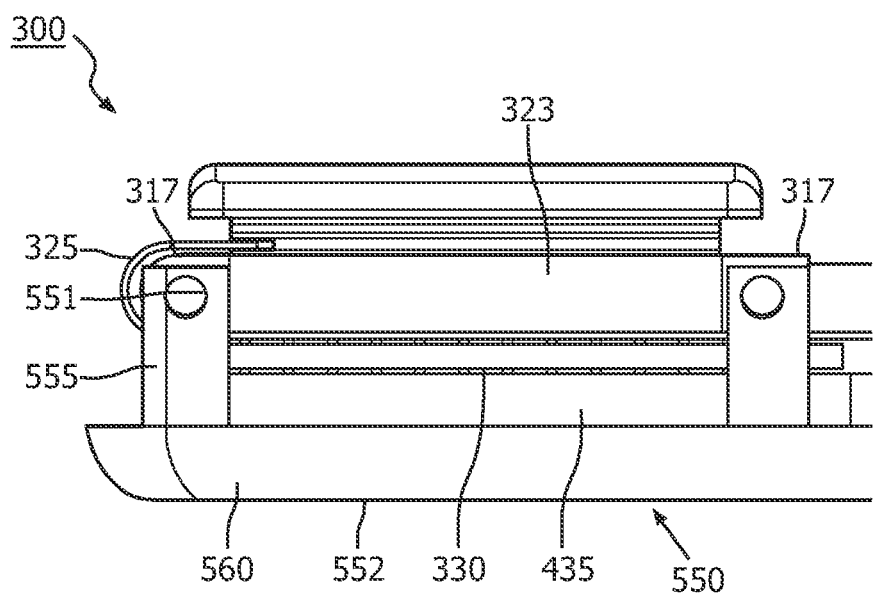
FIG. 3B is a schematic illustration an additional view of the ultrasound probe illustrated in FIG. 3A according to an embodiment of the disclosure.

FIG. 3A is an isometric view of the bottom of the probe 300 with a bolster plate 550 according to an embodiment of the disclosure positioned against the PCB 435. FIG. 3B is a side view of the probe 300 with the bolster plate 550. The bolster plate 550 may be sized to apply a uniform pressure to the interposer 330. In some embodiments, the bolster plate may be adjacent with the PCB 435 and hold the PCB 435 in electrical contact with the flexible circuit 325 through the interposer 330. In some embodiments, the bolster plate 550 may have a lip 560 that extends from a base 552 of the bolster plate 550. The lip 560 may fully or partially enclose one or more components of the probe. As shown in FIGS. 3A-B, the lip 560 partially encloses a portion of the probe 300, for example, a portion of the PCB 435. In some embodiments, the lip 560 may be used for aligning components during assembly. The bolster plate 550 may include one or more tabs 555. The tabs 555 may extend from the base 552 and/or lip 560 of the bolster plate 550. Although two tabs 555 are visible in FIGS. 3A-B, the bolster plate 550 may include two additional tabs on the other side of the probe 300. The additional tabs may be aligned to be symmetric with tabs 555. The tabs 555 may be configured to align the transducer mount 315, interposer 330, and PCB 435. For example, the tabs 555 may have a flat surface disposed against sides of the transducer mount 315, interposer 330, and PCB 435, and positioned to prevent lateral movement of the transducer mount 315, interposer 330, and PCB 435. In the embodiment illustrated in FIGS. 3A and 3B, the tabs 555 have surfaces disposed against longitudinal sides of the transducer mount 315, interposer 330, and PCB 435. In some embodiments, the tabs 555 are configured to be positioned in the notches 317 of the transducer mount. As a result, the step portion 323 is disposed between the tabs 555. The configuration of the tabs 555 in the notches 317 and the step portion 323 between the tabs 555 may further facilitate assembly of the probe 300 and further prevent movement of the transducer mount 315, interposer 330, and PCB 435. Each tab 555 may include an opening 551. The openings 551 may be positioned to align with openings 341 in the transducer mount 315. In some embodiments, the tabs 555 may be omitted, and the lip 560 may extend to at least partially enclose a portion of the transducer mount 315. The lip 560 may include surfaces that are positioned against the sides of one or more of the transducer mount 315, interposer 330, and PCB 435. The lip 560 may include openings that align with openings 341 in the transducer mount 315.

Figure 4A:
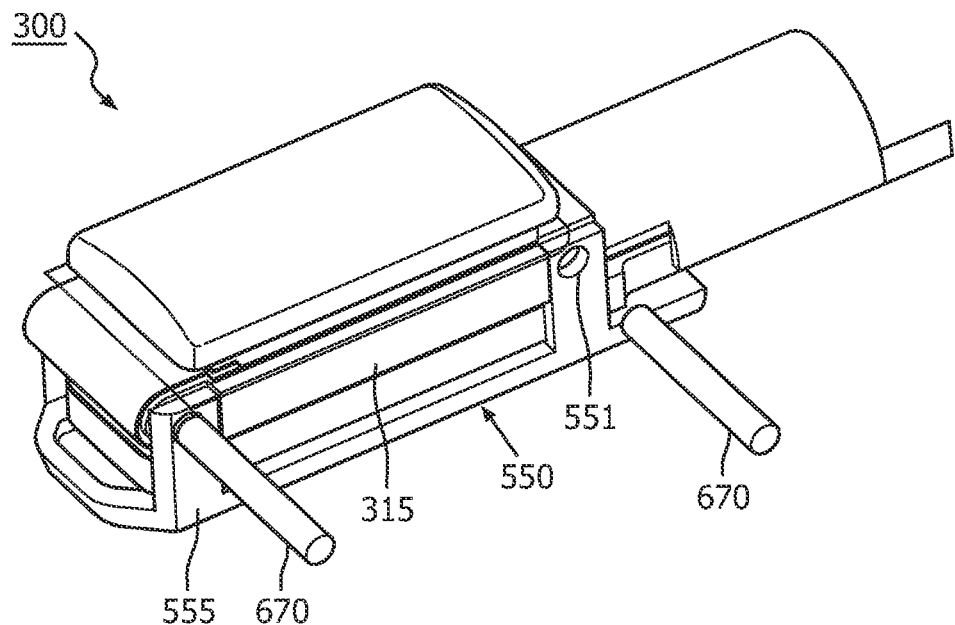
FIG. 4A is a schematic illustration of an exploded view of the ultrasound probe illustrated in FIG. 3A including fasteners according to an embodiment of the disclosure.
Figure 4B:
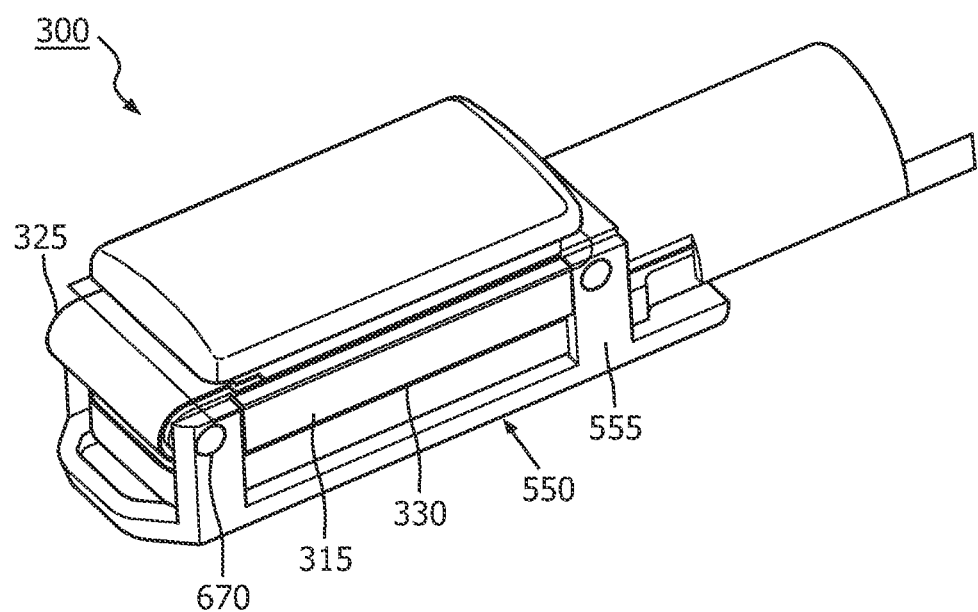
FIG. 4B is a schematic illustration of the ultrasound probe illustrated in FIG. 4A including fasteners according to an embodiment of the disclosure.

FIGS. 4A-B are schematic illustrations of the ultrasound probe 300 with the bolster plate 550 secured to the transducer mount 315 by fasteners 670 according to an embodiment of the disclosure. The fasteners 670 may pass through the openings 551 and openings in the transducer mount 315. FIG. 4B shows the fasteners 670 installed in the probe 300. The fasteners 670 may be used to maintain the bolster plate compressing the printed circuit board 435, interposer 330, and flexible circuit 325 against the transducer mount 315. A variety of fasteners may be used for fasteners 670. Fasteners that may be used include, but are not limited to, pins, screws, and coil spring pins. Coil spring pins may absorb shock and/or vibrations, provide an equal stress distribution around the circumference of the openings in the tabs and transducer mount, and/or a constant radial force. The fasteners 670 may be held in place using a variety of approaches. For example, the fasteners 670 may be held in place by friction, compression, and/or an adhesive. In some embodiments, the fasteners 670 may be flush with the outside surface of the tabs 655.

FIG. 5 is a schematic illustration of a side view of a portion of ultrasound probe 300 according to an embodiment of the disclosure. In some embodiments, the tab 555 of bolster plate 550 (not shown in FIG. 5) may have an opening 551 that is offset from the opening 341 in transducer mount 315 when the bolster plate 550 is positioned. The offset 701 between the openings 341, 551 is indicated by two lines indicated by the arrow. The bolster plate 550 may be compressed against the PCB board 435 to remove the offset 701 and align the openings 341, 551. Fasteners (not shown) may then be inserted into the openings 341, 551 to secure the bolster plate 550 in place. The initial offset 701 between the openings 341, 551 may allow the bolster plate 550 to maintain a compressive force that may provide electrical coupling between the PCB board 435 and the flexible circuit 325 through the interposer 330. In some embodiments, the conductors 335 on upper 331 and lower 332 surfaces of the interposer 330 may be compressible to allow the offset 701 to be removed. While the embodiment of FIG. 5 illustrates the offset in a direction along the length of the tab 555, other embodiments may have the offset in another direction, for example, along a direction that is at an angle relative to the direction of the length of the tab 555.

Figure 6:
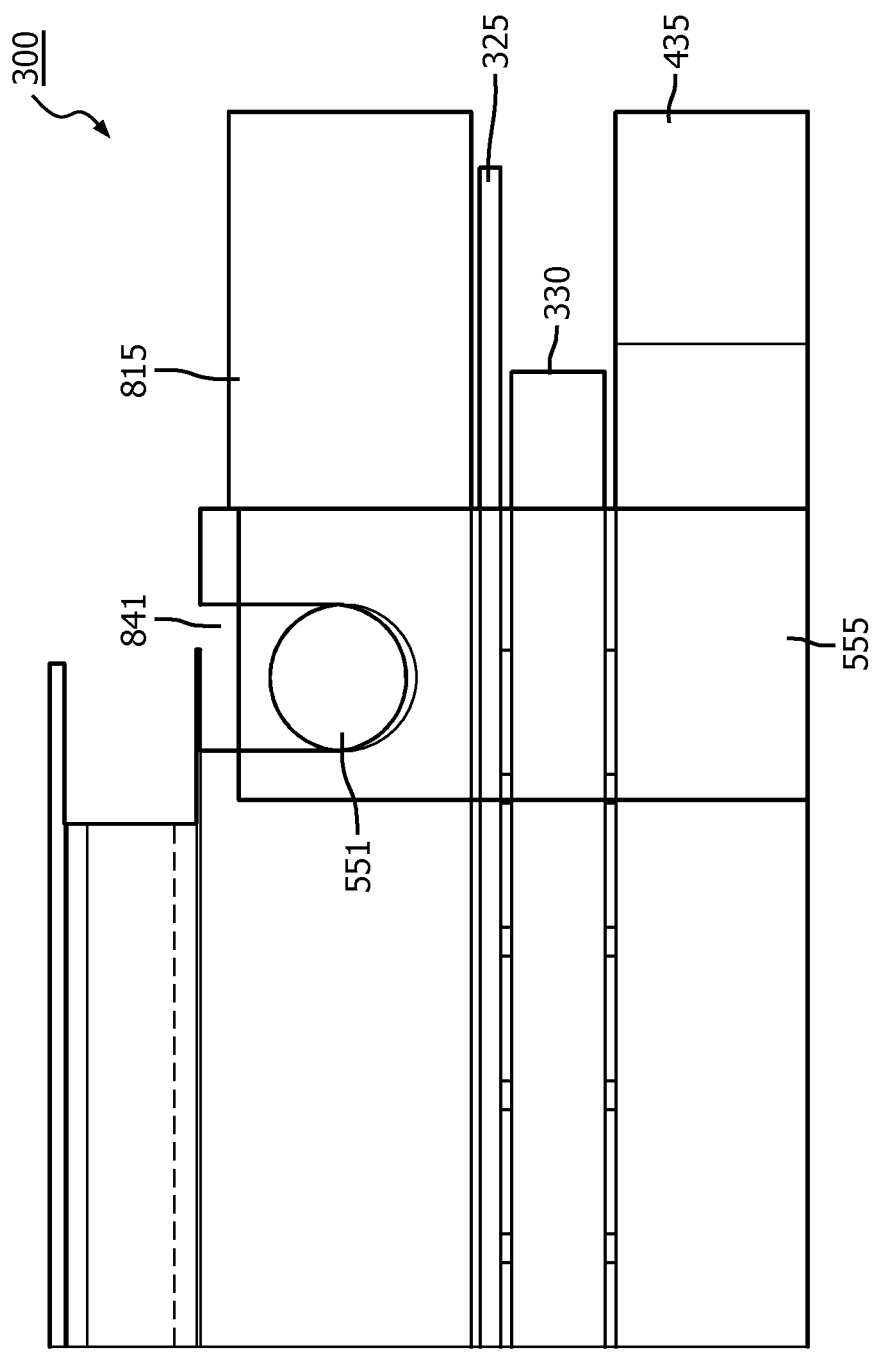
FIG. 6 is a schematic illustration of an ultrasound probe according to an embodiment of the disclosure.

FIG. 6 is a schematic illustration of a side view of a portion of ultrasound probe 300 including a transducer mount 815 according to another embodiment of the disclosure. In some embodiments, a U-shaped slot 841 open to the top of the transducer mount 815 may be included in the probe 300. In some ultrasound probe configurations, the U-shaped slot 841 may be easier to fabricate than a hole enclosed by the transducer mount 815, for example, the opening 341 shown in FIG. 5. An opening 551 in a tab 555 of bolster plate 550 (not shown in FIG. 6) may be positioned to align with the U-shaped slot 841. In some embodiments, the U-shaped slot 841 and opening 551 may be offset to provide compression when the bolster plate is secured with fasteners (not shown) in a similar manner as described in reference to FIG. 5.

In the embodiments illustrated in FIGS. 1-6, a bolster plate may allow an interposer to be utilized to couple a flexible circuit to a PCB without sacrificing surface area on the electrical components for fasteners. The bolster plate may allow fasteners to be offset from the components and/or the acoustical path of a transducer. In some embodiments, the bolster plate may enhance dissipation of heat from the transducer. The bolster plate may be implemented as a metal, a rigid plastic, and/or other suitable material. In some embodiments, the tabs and/or lip may include different materials than the base of the bolster plate. The bolster plate may include additional flanges, tabs, and/or ribs that may facilitate the alignment of components during assembly. The flanges, tabs, and/or ribs may be on an upper surface, lower surface, and/or side of the bolster plate. In some embodiments, an upper surface of the bolster plate adjacent a PCB board may be patterned to improve uniformity of pressure applied to an interposer.

FIGS. 7A-B are schematic illustrations of the ultrasound probe 300 according to an embodiment of the invention. FIG. 7A is an isometric view of the top of probe 300 and FIG. 7B is a side view of the distal end of the probe 300. The probe 300 is enclosed by a protective shell 920. The protective shell 920 may be a metal, polymer, or other suitable material. In some embodiments, the protective shell 920 may be configured to act as a secondary securing mechanism for a bolster plate 950. In some embodiments, the protective shell 920 may protect the internal components of the probe 300 from moisture, electrical interference, dust, and/or biological contamination.

Embodiments of the probes of the present disclosure may be used as a TEE ultrasound probe. A TEE ultrasound probe is often implemented at the distal end of a flexible endoscope-type device. The TEE ultrasound probe may be guided through tortuous cavities within the body for placement for imaging. For example, a TEE probe may be inserted down the esophagus from which the ultrasound transducer may scan the heart for diagnostic imaging and/or monitoring of a medical procedure (e.g., stent placement). Unlike external ultrasound probes, the TEE probe may not have to contend with the chest wall, ribs, or lungs obscuring a view of the heart. The TEE ultrasound probe implemented using an interposer, such as the probes illustrated in FIGS. 1-7, may be less expensive to manufacture and/or more reliable in a clinical environment. The use of an interposer may reduce the number of required soldered connections, which may reduce the number of solder failures between circuits. The bolster plate may provide reliable compression to maintain electrical connections through the interposer during navigation of the TEE probe. A PCB may be more robust than a second flexible circuit, reducing the risk of cracking during probe navigation. The PCB may be capable of providing a larger number and/or variety of electrical circuits than a flexible circuit.

When a TEE ultrasound probe implemented using an interposer is repaired, disassembly may be faster and less costly than a traditional TEE probe having two flexible circuits. No de-soldering of components may be required in some embodiments. Fasteners may be removed from the bolster plate tabs and transducer mount, the bolster plate removed, and the remaining components may then be separated. Once separated, individual components may be repaired, retained, or replaced. The TEE probe may then be reassembled as described in reference to FIGS. 1-4 and returned for use in the clinic.

Although embodiments of the present disclosure have been described with reference to a TEE ultrasound probe, it is also envisioned that the embodiments of the present disclosure can be extended to other ultrasound probes configured for imaging, for example, where limited probe external dimensions may be desired, such as catheter ultrasound probes. Accordingly, the present system may be used to obtain and/or record image information related to, but not limited to renal, testicular, breast, ovarian, uterine, thyroid, hepatic, lung, musculoskeletal, splenic, cardiac, arterial and vascular systems.

Further, the present systems, apparatuses, and methods, may also be extended to any small parts imaging where an interposer may be desired. Suitable ultrasonic imaging systems may include a Philips® ultrasound system which may, for example, support a conventional broadband linear array, two dimensional array, and/or three dimensional array transducer that may be suitable for small-parts imaging.

Figure 8:
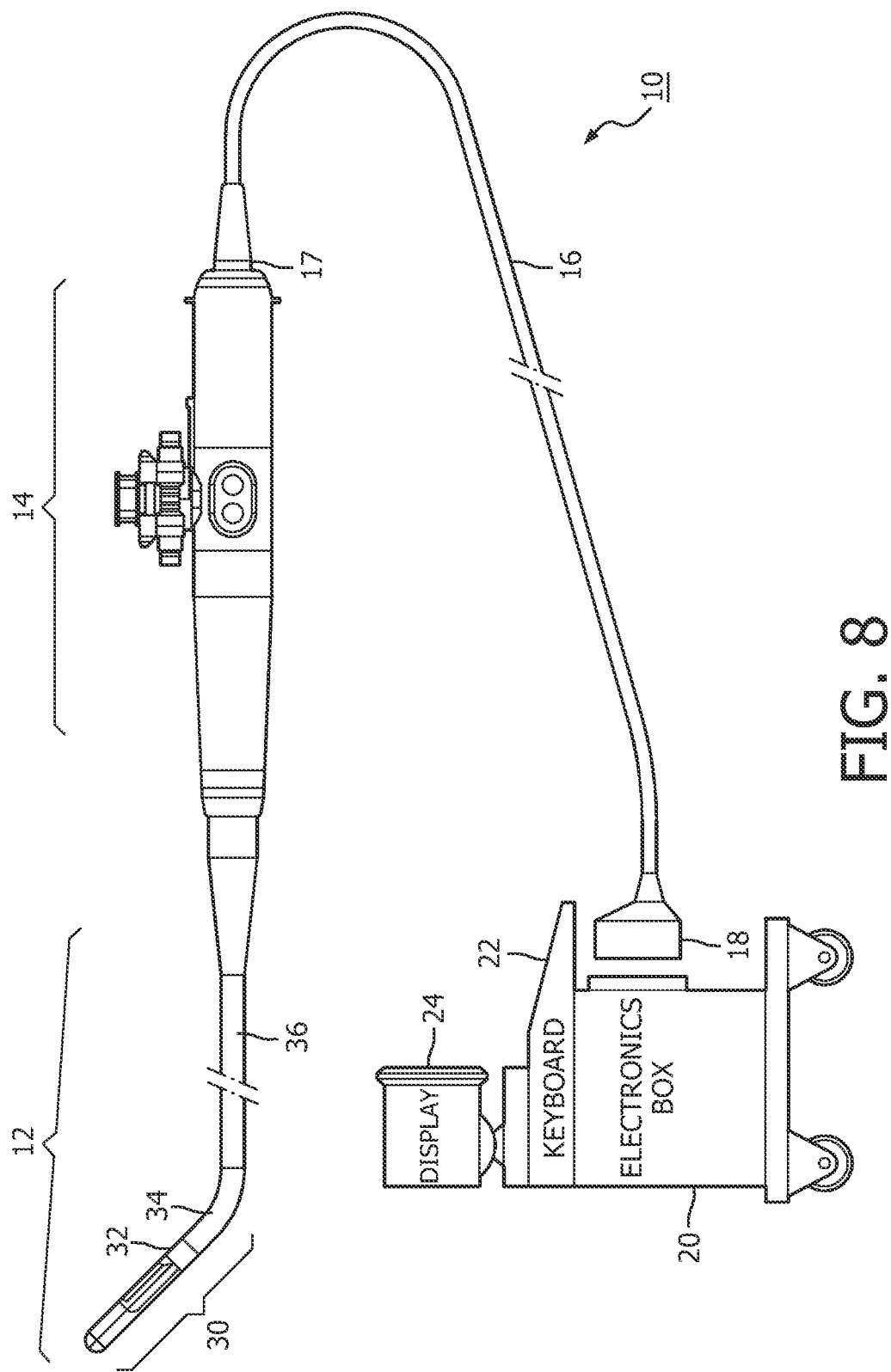
FIG. 8 is a schematic illustration of an ultrasound imaging system according to an embodiment of the disclosure.

An example ultrasound system that may include an ultrasound probe according to an embodiment of the disclosure is illustrated in FIG. 8. The imaging system 10 may be a transesophageal exam (TEE) system. The imaging system 10 may include a TEE probe 12 with a probe handle 14 connected by a cable 16, a strain relief 17, and a connector 18 to an electronics box 20. In some embodiments, TEE probe 12 may be implemented using ultrasound probe 300 illustrated in FIG. 7A-B. The electronics box 20 may interface with a keyboard 22 and provide imaging signals to a video display 24. The electronics box 20 may include a transmit beam former, a receive beam former, and an image generator. The electronics box 20 may further include a volume renderer for three dimensional images, a graphics processor for additional display elements on the video display 24, and/or a B-mode processor for Doppler imaging. The TEE probe 12 may have a distal part 30 connected to an elongated flexible or semi-flexible body 36. The proximal end of elongated part 36 may be connected to the distal end of probe handle 14. Distal part 30 of probe 12 may include a rigid region 32 and a flexible region 34, which may be connected to the distal end of elongated body 36. The probe handle 14 may include a positioning control 15 for articulating flexible region 34 and thus orienting rigid region 32 relative to tissue of interest. The elongated semi-flexible body 36 may be constructed and arranged for insertion into the esophagus.

Figure 9:
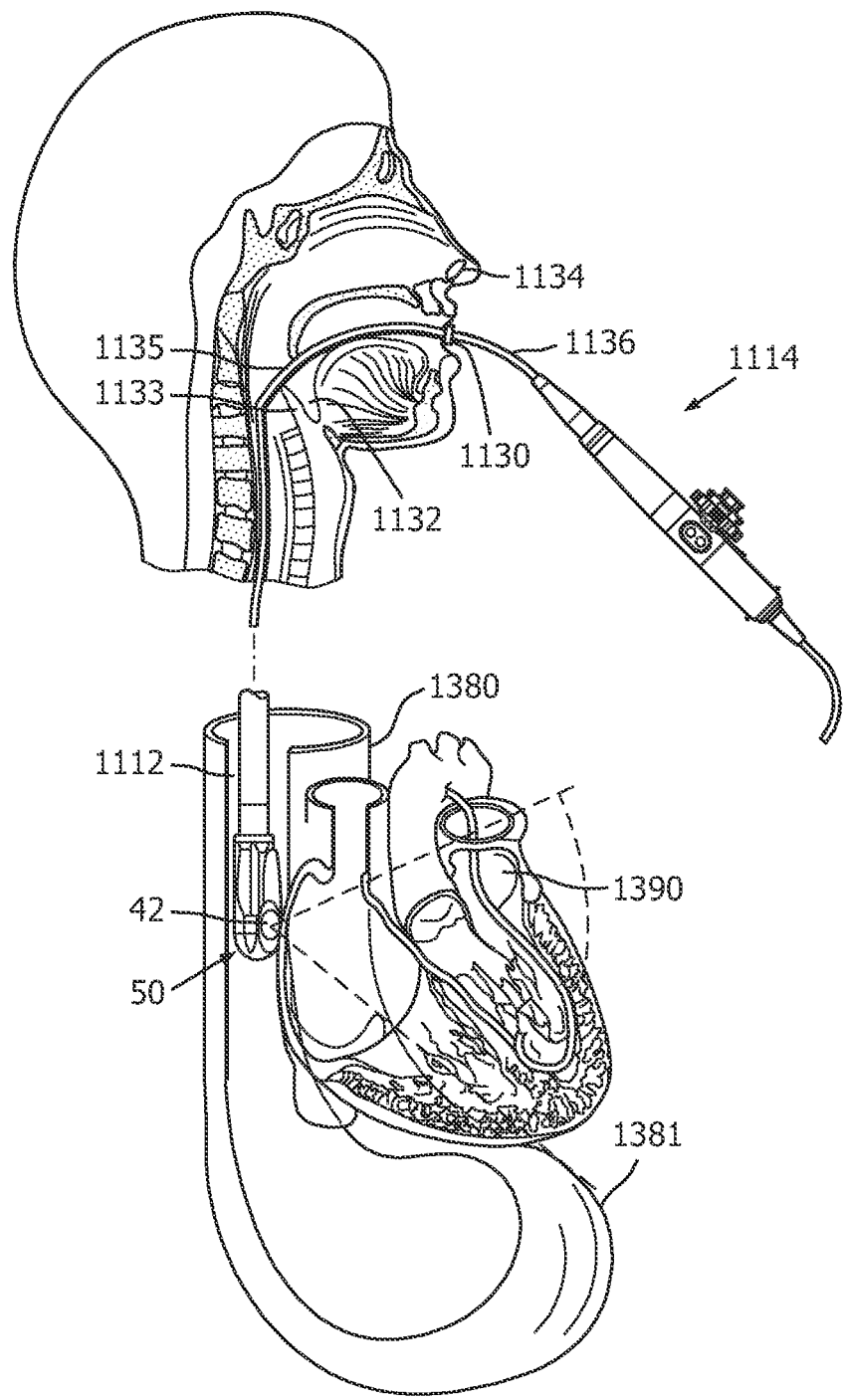
FIG. 9 is a schematic illustration of an ultrasound probe according to an embodiment of the disclosure.

FIG. 9 is a schematic illustration of a TEE probe 1112 used according to an embodiment of the disclosure. The TEE probe 1112 may be implemented using TEE probe 12 and imaging system 10 illustrated in FIG. 8. A clinician may introduce the TEE probe 1112 with an introducer 1135 through the mouth 1130, laryngopharynx 132 into the esophagus 1380. After moving the probe and the introducer past uvula 1133, distal part 50 of the probe 1112 is positioned inside the gastrointestinal (GI) track at a desired location. Alternatively, a clinician introduces the probe 1112 through the nasal cavity 1134 to the esophagus 1380. Distal part 50 with transducer array 42 may be positioned inside the esophagus 1380 as shown or the fundus of the stomach 1381. To image the heart 1390, the transmit beamformer focuses the emitted pulses at desired depths, and the receive beamformer detects echoes from structures in the thoracic cavity.

Figure 10:
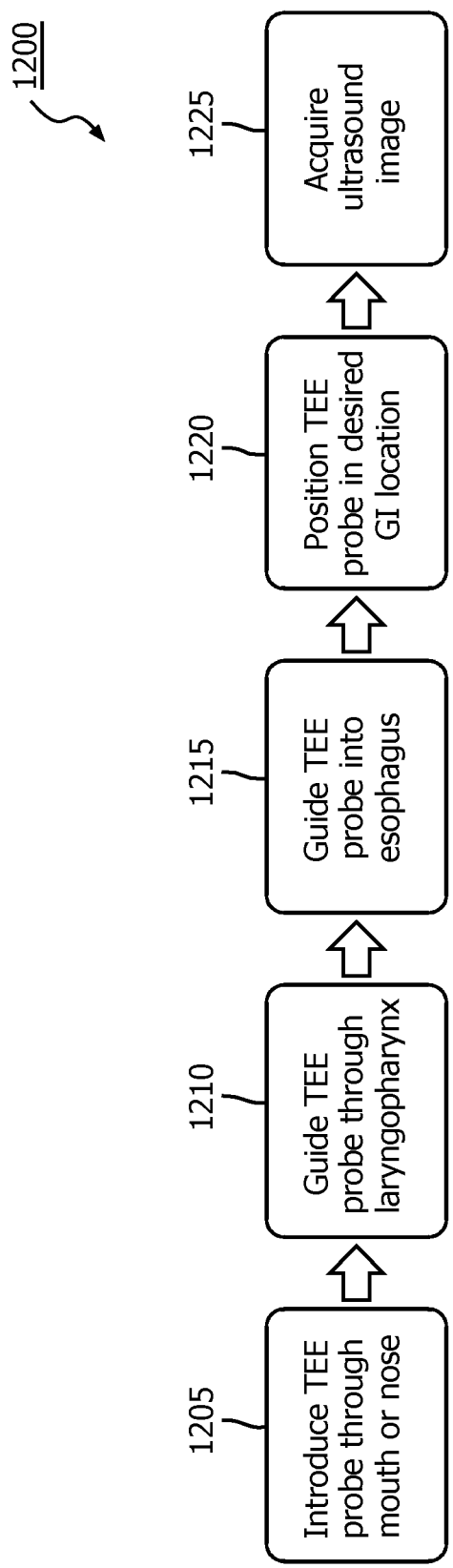
FIG. 10 is a flow chart of a method according to an embodiment of the disclosure.

FIG. 10 is a flow chart of a method 1200 of using a TEE probe according to an embodiment of the invention. In some embodiments, the method may be performed using the TEE probe 1112 illustrated in FIG. 9 or TEE probe 12 and imaging system 10 illustrated in FIG. 8. In Step 1205, the TEE probe may be introduced into a patient through the mouth or nose. The clinician may then guide the TEE probe through the laryngopharynx at Step 1210. The TEE probe may then be guided into the esophagus of the patient at Step 1215. Once in the esophagus, the TEE probe may be positioned to a desired location within the GI track (e.g., portion of esophagus, stomach) at Step 1220. The clinician may then use the TEE probe to acquire an ultrasound image at Step 1225. The image may be of the heart, another organ, and/or a medical device. In some embodiments, ultrasound images may be acquired during Steps 1205-1220. Acquiring images during movement of the TEE probe may assist with guidance and/or positioning of the probe.

Certain additional advantages and features of this invention may be apparent to those skilled in the art upon studying the disclosure, or may be experienced by persons employing the novel system and method of the present invention, chief of which is that a more reliable TEE and catheter ultrasound devices and methods of operation thereof are provided. Another advantage of the present systems and method is that conventional medical image systems can be easily upgraded to incorporate the features and advantages of the present systems, devices, and methods.

Of course, it is to be appreciated that any one of the above embodiments or processes may be combined with one or more other embodiments and/or processes or be separated and/or performed amongst separate devices or device portions in accordance with the present systems, devices and methods.

Finally, the previous discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. An ultrasound probe, comprising:
   an elongate member having a proximal portion and a distal portion configured for insertion into a body lumen of a patient;
   a transducer assembly coupled to the distal portion of the elongate member,
   wherein the transducer assembly comprises:
      a transducer mount comprising:
         a length with a first end and an opposite second end;
         an upper surface; and
         a lower surface;
      a transducer stack coupled to the upper surface of the transducer mount;
      a flexible circuit coupled to the transducer stack and wrapped under the first end of the transducer mount, wherein the flexible circuit covers a portion of the lower surface of the transducer mount;
      an interposer adjacent to the flexible circuit, opposite the lower surface of the transducer mount, wherein the flexible circuit is directly electrically coupled to the transducer stack and the interposer;
      a printed circuit board adjacent to the interposer opposite the flexible circuit and electrically coupled to the flexible circuit through the interposer;
      a bolster plate adjacent to the printed circuit board; and
      a fastener configured to secure the bolster plate to the transducer mount such that the printed circuit board, the interposer, and the flexible circuit are compressed between the bolster plate and the transducer mount, wherein the fastener extends through the bolster plate and into the transducer mount, and wherein the bolster plate is configured to hold the printed circuit board in electrical contact with the flexible circuit through the interposer.

2. The ultrasound probe of claim 1, wherein the bolster plate includes a tab extending from a surface of the bolster plate to the transducer mount, wherein the tab is configured to couple to the transducer mount and the tab having a surface disposed against a side of the transducer mount.

3. The ultrasound probe of claim 2, wherein the tab includes a first opening and the transducer mount includes a second opening, and wherein the fastener is configured to fit within the first and second openings to couple the bolster plate to the transducer mount.

4. The ultrasound probe of claim 1, wherein the fastener extends in a plane parallel to a plane of the transducer stack.

5. The ultrasound probe of claim 1, wherein the fastener is outside an acoustical path of the transducer stack.

6. The ultrasound probe of claim 1, wherein the fastener is a coil spring pin.

7. The ultrasound probe of claim 3, wherein the first opening and the second opening are positioned to be offset from each other and aligned when compression is applied to the bolster plate.

8. The ultrasound probe of claim 3, wherein the second opening is a U-shaped slot.

9. The ultrasound probe of claim 1, wherein the bolster plate includes a lip extending from a perimeter of the bolster plate and at least partially encloses a portion of the printed circuit board.

10. The ultrasound probe of claim 9, wherein at least a tab portion of the lip extends to the transducer mount and includes a first opening, and the transducer mount includes a second opening, and wherein the first and second openings are configured to have the fastener fit within the first and second openings to couple the bolster plate to the transducer mount.

11. The ultrasound probe of claim 1, wherein the transducer mount includes a flange on the lower surface at the second end, wherein the flange is configured to align the printed circuit board with the interposer.

12. The ultrasound probe of claim 1, further comprising a protective shell configured to surround the bolster plate, printed circuit board, interposer, flexible circuit, transducer mount, and a portion of the transducer stack.

13. The ultrasound probe of claim 12, wherein the protective shell is configured to secure the bolster plate to the transducer mount.

14. The ultrasound probe of claim 1, wherein the ultrasound probe is included in an endoscope-type device.

15. The ultrasound probe of claim 10, wherein the flexible circuit is wrapped around the fastener, the first opening, and the second opening.

16. The ultrasound probe of claim 1, wherein the fastener is a screw.

17. The ultrasound probe of claim 1, wherein the transducer mount comprises a width with a first side and an opposite second side, and wherein the fastener extends between the first side to the second side.

* * * * *